United States Patent [19]

Lecuyer

[11] Patent Number: 5,437,627
[45] Date of Patent: Aug. 1, 1995

[54] IMPLANTABLE VALVE FOR THE TREATMENT OF HYDROCEPHALY

[75] Inventor: Alain Lecuyer, Grasse, France

[73] Assignee: Cordis Corporation, Miami Lakes, Fla.

[21] Appl. No.: 121,159

[22] Filed: Sep. 14, 1993

[30] Foreign Application Priority Data

Sep. 15, 1992 [FR] France ................ 92 10972

[51] Int. Cl.6 .................................. A61M 5/00
[52] U.S. Cl. ............................................. 604/9
[58] Field of Search ................ 604/8, 9, 247; 137/539

[56] References Cited

U.S. PATENT DOCUMENTS

| | | | |
|---|---|---|---|
| 3,725,990 | 4/1973 | Peterson et al. | 137/539 |
| 3,886,948 | 6/1975 | Hakim . | |
| 3,889,687 | 6/1975 | Harris et al. . | |
| 3,924,635 | 12/1975 | Hakim . | |
| 4,106,510 | 8/1978 | Hakim et al. . | |
| 4,332,255 | 6/1982 | Hakim et al. . | |
| 4,387,715 | 6/1983 | Hakim et al. | 604/9 |
| 4,540,400 | 9/1985 | Hooven | 604/9 |
| 4,551,128 | 11/1985 | Hakim et al. | 604/9 |
| 4,557,721 | 12/1985 | Hooven | 604/9 |
| 4,595,390 | 6/1986 | Hakim et al. | 604/9 |
| 4,621,654 | 11/1986 | Holter | 604/10 |
| 4,627,832 | 12/1986 | Hooven et al. | 604/9 |
| 4,675,003 | 6/1987 | Hooven | 604/9 |
| 4,676,772 | 6/1987 | Hooven | 604/9 |
| 4,681,559 | 7/1987 | Hooven | 604/9 |
| 4,714,458 | 12/1987 | Hooven | 604/9 |
| 4,714,459 | 12/1987 | Hooven | 604/9 |
| 4,729,762 | 3/1988 | Doumenis | 604/10 |
| 4,741,730 | 5/1988 | Dormandy, Jr. et al. | 604/8 |
| 4,769,002 | 9/1988 | Hooven | 604/9 |
| 4,776,838 | 10/1988 | Sainte-Rose et al. | 604/9 |
| 4,776,839 | 10/1988 | Doumenis | 604/9 |
| 4,781,672 | 11/1988 | Hooven | 604/9 |

Primary Examiner—Jerome L. Kruter
Attorney, Agent, or Firm—Lockwood, Alex, Fitzgibbon & Cummings

[57] ABSTRACT

An implantable valve for the treatment of hydrocephaly is disclosed. The valve includes at least one chamber including a fluid flow orifice capable of being connected to an area within the patient to be drained. The flow orifice is located within a flexible diaphragm which is capable of deforming in response to pressure variations across the valve to compensate for normal variations in pressure and thereby avoid hyperdrainage. The flow orifice is surrounded by a valve seat to receive a spherical member for closing off the flow of fluid therethrough when the pressure differential across the valve is below a predetermined opening pressure. An outflow orifice is configured for connection to a drainage area within the body of the patient and is in fluid communication with the flow orifice to drain excess cerebrospinal fluid when necessary.

16 Claims, 2 Drawing Sheets

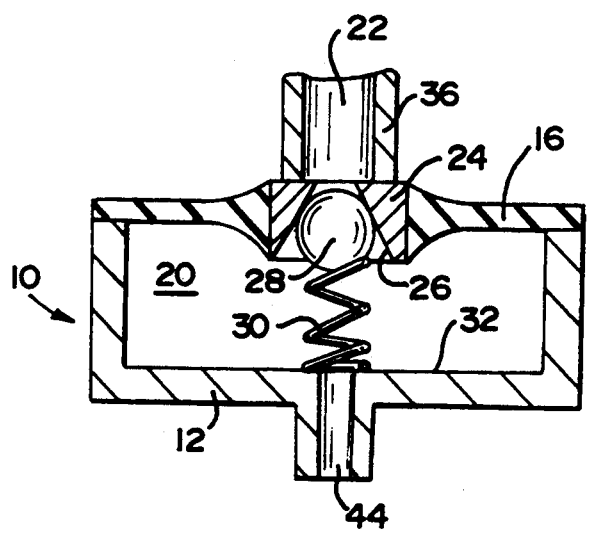
FIG. 2a
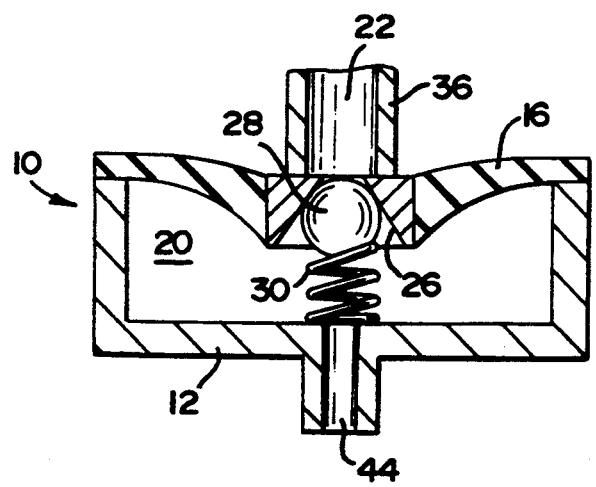
FIG. 2b
FIG. 3
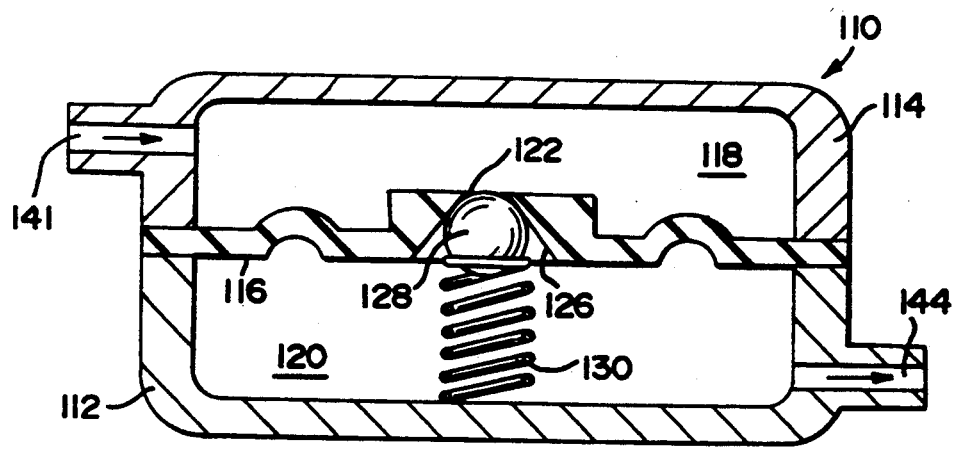

IMPLANTABLE VALVE FOR THE TREATMENT OF HYDROCEPHALY

The present invention relates to medical devices effective in the treatment of hydrocephaly. More specifically, the invention relates to an implantable valve for draining excess cerebrospinal fluid ("CSF") from the brain to a drainage area elsewhere in the body. The valve includes first and second chambers. The first chamber includes a fluid flow having an inlet orifice adapted for fluid communication with the area within the body of the patient to be drained. The orifice is surrounded by a valve seat which receives a valving mechanism for controlling the flow of fluid through the orifice. A resilient member, such as a spring or the like, is positioned within the chamber to maintain the valving mechanism securely within the valve seat, thereby preventing fluid flow through the orifice when the differential pressure across the valve is less than a predetermined minimum opening pressure. A fluid outlet in the chamber is adapted for fluid communication with a suitable drainage area within the body.

BACKGROUND AND BRIEF DESCRIPTION OF THE INVENTION

Hydrocephaly is a condition in which the body, for any of several reasons, is unable to relieve itself of excess CSF collected in the ventricles of the brain, resulting in increased epidural and intradural pressures. This in turn causes adverse physiological effects including compression of brain tissue, impairment of blood flow in the brain tissue and impairment of the brain's normal metabolism.

Drainage valves for the treatment of hydrocephaly are known. Such valves control the drainage of excess CSF from the ventricles of the brain to a suitable drainage location elsewhere in the body such as the peritoneal cavity. CSF drainage valves include check valves, servo valves and combinations thereof. Check valves, for example, operate by opening when the fluid pressure differential between the inlet and outlet openings of the valve exceeds a predetermined threshold value. When opened, the valve allows CSF drainage and thereafter prevents the differential fluid pressure from exceeding the threshold value.

The art, however, has generally failed to provide a valve mechanism for CSF valves to compensate for the differences in liquid column height that occur when the patient rises from a recumbent position. In such a situation, the differential fluid pressure normally increases because of a resulting increased vertical height of the fluid column between the patient's head and the selected drainage location elsewhere in the patient's body. Although such an increase in differential pressure is normal, a check valve, for example, will typically respond by opening and thereby allowing undesired hyperdrainage of the ventricular spaces and possibly causing a potentially serious hematoma. Accordingly, it is desirable to provide an implantable pressure relief valve for the treatment of hydrocephaly which is effective in shunting CSF in response to abnormal intracranial pressures while avoiding hyperdrainage in the event of normal variations in fluid pressure.

The present invention is directed to an implantable valve designed to remedy the aforementioned problems and drawbacks of the prior art by providing a valve having a valving mechanism which allows CSF drainage only when the pressure differential between the area of the brain to be drained and the drainage location in the body exceeds a predetermined threshold value.

The valve of the present invention includes a deformable diaphragm housed within a hermetically sealed unit. The unit includes inlet and outlet ports for the passage of CSF therethrough. The diaphragm includes a fluid flow orifice to direct the flow of CSF from the inflow port through the orifice and to the outflow port for drainage. A valving mechanism is positioned within the fluid flow orifice and includes a spherical member or ball seated within a tapered or conical valve seat. The ball is retained within the seat under the force exerted by a compression spring which coacts with the ball to keep the valve in a closed condition when the valve experiences normal variations in CSF pressure.

Variations in the pressure differential across the valve caused by changes in the fluid column height, such as when the patient arises from a lying or recumbent position, are compensated for by the action of the flexible diaphragm. Such normal pressure variations will cause a pressure variation across the valve which deforms the diaphragm slightly while maintaining the ball within the conical seat in the fluid flow orifice. Excessive intracranial pressures, however, will cause the valve to open by exerting additional force directly against the ball and the compression spring. Compression of the spring will unseat the ball and thereby open the valve to allow CSF to flow through the orifice to the outflow port and to a suitable drainage location.

In one embodiment of the invention, the diaphragm divides the valve housing into first and second chambers. The first chamber is associated with the inflow port on the valve and is maintained at ambient pressure while the second or outflow chamber is maintained at a pressure equivalent to the pressure of the drainage location within the body. Flexible tubing connects the fluid flow orifice within the diaphragm to the inflow port in the first chamber to maintain the valve seat and the ball seated therein at intracranial pressures. In this arrangement, the ball remains firmly seated within the valve seat as long as the pressure differential across the valve remains at a substantially constant predetermined value. Differences in fluid column height are compensated for by flexing of the diaphragm while the ball remains firmly seated within its valve seat.

In a second embodiment, the valve is again provided within a hermetically sealed housing having first and second chambers. The first chamber is in fluid communication with the inflow port on the valve. The second chamber is in fluid communication with the outflow port for drainage of excess CSF. The first chamber is maintained at the fluid pressure of the CSF source location while the second chamber is maintained substantially at the fluid pressure of the drainage location. Pressure differentials across the diaphragm will cause both the flexible diaphragm to become deformed and, when the pressure differential exceeds a first predetermined threshold value, the ball member will be unseated to open the fluid flow orifice between the first and second chambers, thereby allowing drainage of CSF.

It is accordingly an object of the present invention to provide a device for the relief of excess cerebrospinal fluid pressure for use in the treatment of hydrocephaly and the like.

It is another object of the present invention to provide a drainage valve suitable for cranial implantation and useful in the treatment of hydrocephaly.

It is another object of the present invention to provide a drainage valve useful in the treatment of hydrocephaly and which prevents excess drainage of CSF in the event of normal increases in differential fluid pressures such as when the patient arises from a recumbent position, for example.

These and other objects of the present invention will be more clearly understood by those skilled in the art following a consideration of the remainder of the disclosure, including the detailed description of the preferred embodiments and the appended claims.

BRIEF DESCRIPTION OF THE DRAWINGS

FIG. 2a is a side elevational view, in cross-section, schematically illustrating the valve of FIG. 1 in one aspect of its operation;

FIG. 2b is a side elevational view, in cross-section, of the valve of FIG. 1, schematically depicting the operation of the aforementioned valve in another aspect of its operation; and FIG. 3 is a side elevational view, in cross-section, of an implantable valve according to a second embodiment of the invention.

DETAILED DESCRIPTION OF THE PREFERRED EMBODIMENTS

Figure 1:
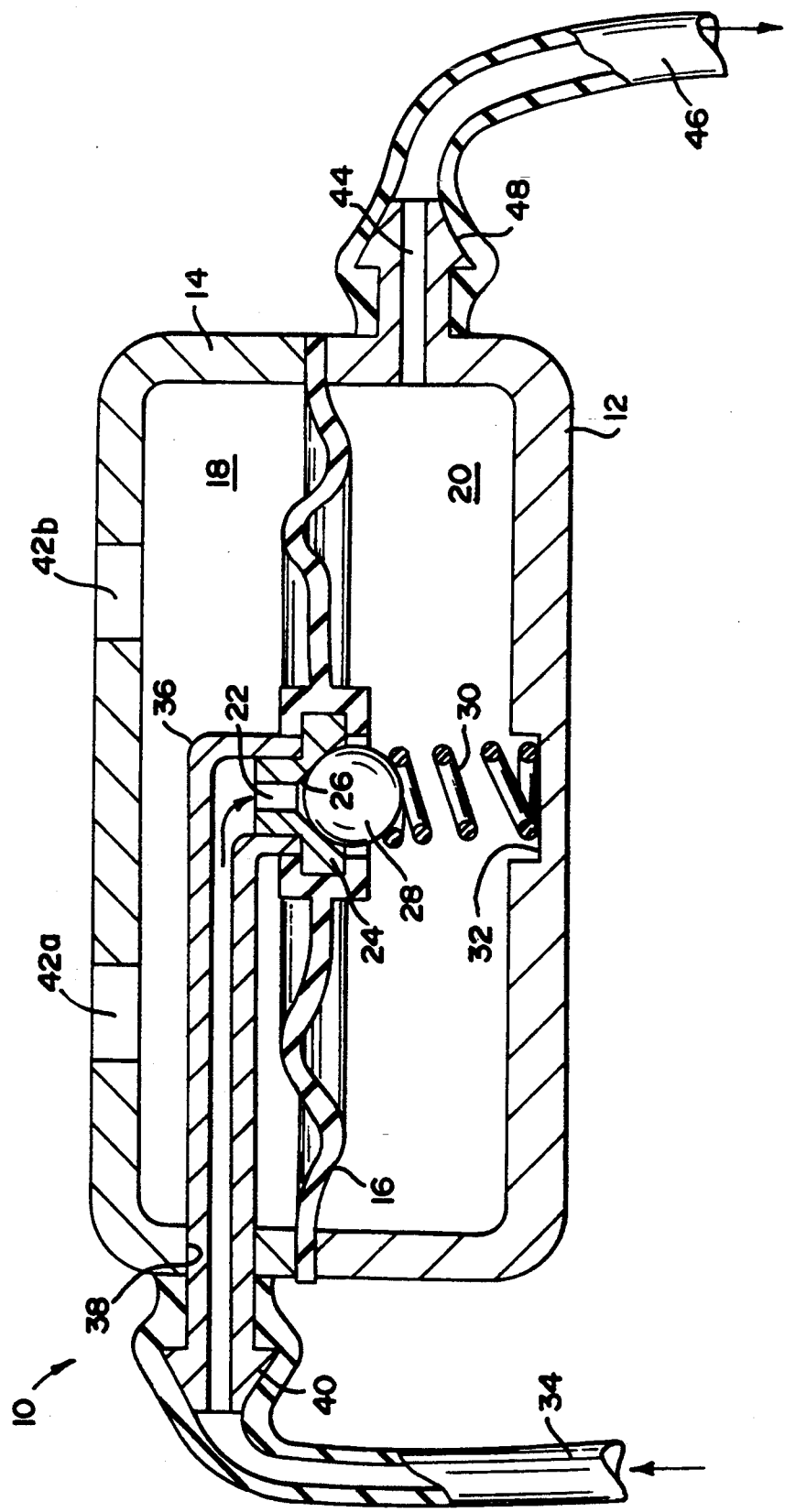
FIG. 1 is a side elevational view, in cross-section, of an implantable valve according to a first embodiment of the invention.

The present invention provides an implantable valve for the controlled drainage of CSF from a ventricle in the brain to a suitable drainage location elsewhere in the body. The interior of the valve housing is separated into first and second chambers by a flexible diaphragm having a fluid flow orifice extending therethrough to permit fluid communication between the inflow port of the valve and the outflow port. A conical valve seat is positioned within the fluid flow orifice and a spherical member or ball is seated and held within the valve seat by a compression spring. The spring, ball and valve seat function as a ball valve which coacts with the flexible diaphragm to prevent drainage of CSF under normal conditions while allowing excess CSF to flow through the valve in response to fluid pressure differentials arising from an excessive build up of CSF pressure within the brain. The diaphragm is adapted to deform in response to normal pressure differentials across the valve and the ball valve and the diaphragm coact to maintain the valve in a closed condition during normal pressure variations across the valve while also allowing excess CSF to flow through the orifice when intracranial pressures cause a pressure differential across the valve in excess of a preset threshold value or "popping" pressure.

In describing the preferred embodiments of the invention, reference is now made to the various figures wherein structural elements are indicated by reference numerals and wherein like reference numerals indicate like structures.

FIG. 1 illustrates a first preferred embodiment of the invention. The valve 10 includes a housing having bottom and top portions 12 and 14, respectively. A flexible diaphragm 16 separates the interior of the valve into a first chamber 18 and a second chamber 20. A fluid flow orifice 22 extends through the diaphragm 16 and is configured to receive a valving piece 24 therein. The valving piece 24 includes a conical valve seat 26 which diverges into the second chamber 20, substantially as shown in FIG. 1. The seat 26 allows fluid communication between the two chambers 18 and 20 under certain conditions, as is more fully explained herein.

A spherical member 28 is configured to be seated within the diverging portion of the conical valve seat 26. A compression spring 30 is positioned on the bottom wall 32 of the second chamber 20 and in registry with the flow orifice 22. The compression spring 30 bears against the spherical member 28 to retain the member 28 within the conical valve seat 26, thereby maintaining the valve 10 in a closed condition when the pressure differential between the chambers 18 and 20 is less than a predetermined popping pressure.

An inflow catheter 34 permits fluid communication between a ventricle in the patient's brain (not shown) and the valve 10. Flexible tubing 36 extends from the upstream portion of the valving piece 24 through an aperture 38 in the upper housing 14. A locking connection 40 is provided at the upstream end of the tubing 36 and is configured to be received within the downstream end of the catheter 34, thereby establishing fluid communication between the inflow catheter 34 and the fluid flow orifice 22.

In this arrangement of parts, the fluid pressure exerted against the spherical member 28 is maintained at a first pressure substantially equivalent to the fluid pressure within the ventricle where the inflow catheter 34 is inserted. First chamber 18, however, is maintained at a second or ambient pressure which is substantially equivalent to the subcutaneous or ambient pressure. To maintain the pressure in the first chamber 18 at ambient pressures, pressure-equalizing apertures 42a, 42b are provided in the upper housing member 14. Meanwhile, the second chamber 20 is maintained at a third pressure substantially equivalent to the pressure of the drainage area (not shown) in fluid communication with the second chamber 20 through the outflow port 44. The outflow port is secured to the drainage catheter 46 with a locking connector 48 extending from bottom housing member 12. The drainage catheter 46 directs the flow of CSF to a selected drainage area, as known by those skilled in the art.

Referring to FIGS. 2a and 2b, the second chamber 20 of the above-described embodiment is diagrammatically shown and the operation thereof will now be described. FIG. 2a depicts the valve 10 in a "normal" configuration such as when the patient is lying down or in a reclined position with the pressure in the lower chamber 20 at ambient pressure and the flexible diaphragm 16 in an unstressed condition. The compression spring 30 is positioned within the second chamber 20 and is configured to exert sufficient force against the spherical member 28 to retain the spherical member 28 within the valve seat 26 when the pressure differential across the valve 10 is less than a predetermined opening or popping pressure. When the pressure across the valve exceeds the aforementioned popping pressure, the increased liquid pressure within the ventricle of the brain will force the spherical member 28 downward against the compression spring 30, thereby opening the orifice 22 and allowing CSF to pass through the orifice 22 and into the second chamber 20. The excess CSF will then pass through the outflow port 44 to the designated drainage area within the body.

The interaction between the valving means of the valve seat 26, the spring 30 and the spherical member 28 with the flexible diaphragm 16 is illustrated in FIG. 2b. A sudden change in the liquid column height such as when the patient sits or stands up after being in a lying or recumbent position, causes a pressure drop to occur within the second chamber 20. In other valves, this may cause an undesired hyperdrainage of the ventricle by causing the valving mechanism to open in response to this change in liquid column height. In the valve 10, however, the diaphragm 16 will deform toward the inside of the second chamber 20, substantially as shown in FIG. 2b. Consequently, the diaphragm and the attached valve seat 26 will further compress the spherical member 28 against the spring 30 to prevent the flow of CSF through the orifice 22.

It will be appreciated that the pressure within the second chamber 20 will be less than the ambient pressure, so that the differential pressure across the valve 10 in FIG. 2b will be substantially the same as the condition illustrated in FIG. 2a as long as the characteristics of the diaphragm and the spring 30 have been suitably chosen, as is within the skill of those in the art. Should drainage of CSF be required, excessive CSF pressure exerted against the spherical member 28 will unseat the spherical member and open the orifice 22 to allow CSF to drain therethrough. In this manner, the diaphragm 16 and the above described valving mechanism coact to compensate for normal pressure variations within the valve 10 while also allowing for excess CSF to be drained from the ventricle when abnormal pressure differentials across the valve exceed a predetermined opening pressure.

Referring now to FIG. 3, a second embodiment of the invention is shown. The valve 110 includes components analogous to those described above in connection with the first preferred embodiment of FIG. 1. The valve 110 of FIG. 3 includes upper and lower housing sections 114 and 112, respectively, and a flexible diaphragm 116 separating the interior of the valve 110 into first and second chambers 118, 120. A fluid flow orifice 122 is provided within the diaphragm 116 to connect the two chambers 118 and 120. The orifice 122 is configured to include a conical valve seat 126 which diverges to its widest extent into the second chamber 120. A spherical member 128 is positioned within the valve seat 126 and is retained therein by a compression spring 130 to prevent the flow of fluid through the valve when the pressure differential across the valve 110 is less than the predetermined opening pressure. Inflow port 141 is in fluid communication with a ventricle in the brain and permits CSF to flow from the aforementioned ventricle and into the first chamber 118. Outflow port 144 maintains the second chamber 120 of the valve 110 in fluid communication with the drainage area elsewhere in the body to allow drainage of excess CSF fluid.

The embodiment of FIG. 3 differs from the embodiment of FIG. 1 in that the first chamber 118 of the valve 110 of FIG. 3 is maintained at a first pressure substantially equivalent to the fluid pressure within the ventricle of the brain which is to be drained. The first and second chambers 118 and 120 are maintained in direct fluid communication through the fluid flow orifice 122.

The surface of the diaphragm 116 within the first chamber 118 experiences the pressure variations caused by changes in CSF pressure. In the absence of a pressure differential across the valve 110 in excess of a predetermined popping pressure, the spherical member 128 is retained within the valve seat 126 by the compression spring 130 to prevent the flow of CSF through the flow orifice 122. The diaphragm 116 coacts with the valving mechanism of the conical seat 126, the spherical member 128 and the compression spring 130 so that normal variations in the differential pressure across the valve 110 do not cause drainage of CSF. In this arrangement of parts, the diaphragm 116 deflects downwardly under the influence of a negative pressure in the drainage area such as will be experienced when a patient arises from a reclined position. The aforementioned deflection of the diaphragm 116 compensates for the change in liquid column height while the compression spring 130 and the spherical member 128 maintain a fluid-tight seal within the valve seat 126 to prevent the flow of CSF through the orifice 122, thereby avoiding hyperdrainage.

As with the embodiment of FIG. 1, a build up of CSF will cause the pressure within the first chamber 118 to increase to a point where the pressure differential across the valve 110 exceeds a predetermined popping pressure of the valving mechanism. The excess pressure within the first chamber 118 will unseat the spherical member 128 by forcing it further into the second chamber 120, thereby allowing CSF to flow through the orifice 122, into the second chamber 120 and through the outflow port 144 to a suitable drainage area within the body.

While the valve 110 of FIG. 3 is slightly more complex in its operation than the valve 10 of FIG. 1, those skilled in the art will appreciate that the valve 110 is simpler in its construction, less expensive and easier to manufacture than the valve 10 of FIG. 1. Additionally, the valve 110 of FIG. 3 avoids some of the complications, as known to those skilled in the art, of having the interior mechanism of the valve in contact with the surrounding environment.

While the preferred embodiments of the present invention has been discussed and described in detail above, those skilled in the art will appreciate that various changes and modifications to these embodiments are possible and that such changes can be made without departing from the true spirit and scope of the invention, as defined in the following claims.

I claim:

1. An implantable valve for the treatment of hydrocephaly, comprising:
   a chamber defined by four walls;
   a flexible diaphragm mounted within said chamber and including a fluid flow orifice extending therethrough, said fluid flow orifice is in fluid communication with an inlet capable of being connected to an area within a living patient for drainage thereof;
   a valve seat surrounding said fluid flow orifice;
   a valving mechanism configured to be seated within said valve seat to prevent the flow of fluid through said fluid flow orifice;
   elastic means for retaining said valving mechanism within said valve seat;
   an outlet port capable of being connected to a drainage area within a living patient; and
   a cover member overlies said diaphragm and has an aperture therein to subject a surface of the diaphragm to subcutaneous pressure and to maintain said surface at subcutaneous pressure.

2. The valve as defined in claim 1 wherein said valving mechanism is a ball and said seat is conical.

3. The implantable valve of claim 1 wherein said elastic means is a compression spring.

4. The implantable valve of claim 1 wherein a surface of said diaphragm is subjected to the pressure in the area to be drained.

5. The implantable valve of claim 4 further comprising a cover member overlying said diaphragm, said cover member defining a second chamber.

6. A surgically implantable valve for controlling the passage of cerebrospinal fluid from one location of the body to another location, comprising:
- a housing;
- a flexible diaphragm positioned within said housing, said diaphragm defining at least one chamber within said housing for the passage of cerebrospinal fluid therethrough;
- a fluid flow orifice within said housing and configured to establish fluid communication with the one location;
- an outlet port in said housing configured to establish fluid communication between said chamber and the other location;
- valving means to control the passage of cerebrospinal fluid from said fluid flow orifice to said outlet port, said valving means including a valve seat surrounding said fluid flow orifice and a valving member configured to cooperate with said valve seat to prevent the flow of fluid through said orifice;
- retaining means within said chamber to maintain said valving means in a closed condition when the pressure differential across the valve is less than a predetermined value and in an opened condition when the pressure differential across the valve is equal to or greater than said predetermined value;
- said diaphragm configured to cooperate with said valving member and said retaining means with said diaphragm flexing in response to pressure differentials across the valve to thereby maintain said orifice in a closed condition when said pressure differential is less than said predetermined value;
- a fluid control component that maintains said fluid flow orifice in fluid communication with the one location; and
- pressure control means for maintaining the fluid pressure within said chamber at one pressure level while maintaining the fluid pressure outside said chamber at a different pressure level.

7. The surgically implantable valve of claim 6 wherein said fluid control component is a tube for directing the flow of cerebrospinal fluid from the one location and into said orifice.

8. The surgically implantable valve of claim 6 wherein said pressure control means includes at least one aperture within said housing to expose at least a portion of said diaphragm to ambient pressures.

9. The surgically implantable valve of claim 6 wherein said diaphragm defines first and second chambers within said housing, said first chamber including an inlet flow port to establish fluid communication between said one location and said fluid flow orifice, said second chamber including an outflow port to establish fluid communication between said orifice and said other location.

10. The surgically implantable valve of claim 6 wherein said chamber further includes at least one pressure equalizing aperture as said pressure control means to maintain said chamber at ambient fluid pressures, and a tubular member as said fluid control component to establish fluid communication between an inlet flow port and said fluid flow orifice.

11. The surgically implantable valve as defined in claim 6 wherein said valving means and said retaining means define a ball valve, said valve seat including a conical portion diverging into said chamber and said valving member being spherically configured, said retaining means including a spring positioned within said chamber and operatively associated with said valving member to retain said valving member within said valve seat and maintain said orifice in a closed condition when the pressure differential across the valve is less than a predetermined value.

12. A surgically implantable valve for controlling the passage of cerebrospinal fluid from one location in the body to another location, comprising:
- a housing with a fluid inlet and a fluid outlet, said housing having first and second interior chambers;
- a flexible diaphragm separating said first and said second interior chamber;
- a fluid flow orifice within said diaphragm configured to establish fluid communication between said first and said second chambers, said orifice including a conical valve seat diverging from said first chamber to said second chamber;
- a valving member configured to be retained within said valve seat to halt the flow of cerebrospinal fluid through said orifice;
- retaining means in operative association with said valving member and positioned in said second chamber to maintain said orifice in a closed condition when the pressure differential between said first and said second interior chambers is less than a predetermined opening pressure and in an opened condition when said pressure differential is equal to or greater than said predetermined opening pressure; and
- said diaphragm is configured to cooperate with said valving member and said retaining means, said diaphragm deforming in response to pressure differentials between said first and said second chambers to thereby maintain said orifice in a closed condition when said pressure differential is less than said predetermined opening pressure.

13. The surgically implantable valve of claim 12, further comprising:
- fluid control means for maintaining said fluid flow orifice in fluid communication with the one location; and
- pressure control means for maintaining the fluid pressure within said first chamber at a first pressure while maintaining the fluid pressure within said second chamber at a second and different pressure.

14. The surgically implantable valve as defined in claim 13 wherein said fluid control means is a tubular member for directing the flow of cerebrospinal fluid from the one location and into said fluid flow orifice.

15. A surgically implantable valve as defined in claim 13 wherein said pressure control means includes at least one aperture within said housing to maintain said first chamber at ambient fluid pressures.

16. The surgically implantable valve as defined in claim 12 wherein said first chamber includes an inlet flow port to establish fluid communication between said one location and said first chamber and, wherein said second chamber includes an outflow port to establish fluid communication between said second chamber and said other location.

* * * * *